United States Patent
Bill

(10) Patent No.: US 10,319,477 B1
(45) Date of Patent: Jun. 11, 2019

(54) DYNAMIC DATA-DRIVEN BIOLOGICAL STATE ANALYSIS

(71) Applicant: Virta Health Corp., San Francisco, CA (US)

(72) Inventor: David Bill, San Francisco, CA (US)

(73) Assignee: Virta Health Corp., San Francisco, CA (US)

(*) Notice: Subject to any disclaimer, the term of this patent is extended or adjusted under 35 U.S.C. 154(b) by 0 days.

(21) Appl. No.: 15/453,653

(22) Filed: Mar. 8, 2017

(51) Int. Cl.
| | |
|---|---|
| *G16H 50/20* | (2018.01) |
| *G06N 7/00* | (2006.01) |
| *G01N 33/66* | (2006.01) |
| *G01N 33/64* | (2006.01) |
| *G01N 33/92* | (2006.01) |
| *G06F 19/00* | (2018.01) |

(52) U.S. Cl.
CPC ............ *G16H 50/20* (2018.01); *G01N 33/64* (2013.01); *G01N 33/66* (2013.01); *G01N 33/92* (2013.01); *G06F 19/3456* (2013.01); *G06F 19/3475* (2013.01); *G06N 7/005* (2013.01); *G01N 2800/7066* (2013.01)

(58) Field of Classification Search
CPC ....... G06F 19/345; G06F 17/00; G01N 33/64; A61B 5/0002; A61B 5/7275; G16H 15/00; G16H 50/20
USPC .......................................................... 705/2
See application file for complete search history.

(56) References Cited

U.S. PATENT DOCUMENTS

| | | | | |
|---|---|---|---|---|
| 2003/0233250 A1* | 12/2003 | Joffe | ...................... | G16H 15/00 705/2 |
| 2007/0106127 A1* | 5/2007 | Alman | ................. | A61B 5/0002 600/300 |
| 2008/0234377 A1* | 9/2008 | Ellis | ..................... | A61K 31/202 514/560 |
| 2010/0113892 A1* | 5/2010 | Kaput | ................. | G06F 19/3475 600/301 |
| 2016/0262666 A1* | 9/2016 | Nyberg | ............... | A61B 5/1477 |

FOREIGN PATENT DOCUMENTS

WO   WO-2011088044 A2 *  7/2011  ............. G06F 19/24

* cited by examiner

*Primary Examiner* — Hiep V Nguyen
(74) *Attorney, Agent, or Firm* — Fish & Richardson P.C.

(57) ABSTRACT

In some implementations, a system is capable of obtaining and processing both actively monitored and passively monitored data in parallel in order to improve the accuracy and the specificity by which pathological risks are identified for a user. Data indicating measured levels of one or more metabolic biomarkers and activity data associated with a user is obtained. A biological state for the user is determined based on the measured levels of the one or more metabolic biomarkers. One or more user inputs indicated within the activity data, and scores reflecting respective likelihoods that a particular user input indicates a change to one or more aspects of the biological state for the user for each of the one or more user inputs is determined. Data corresponding to the biological state for the user is then adjusted. A communication that is generated based on the adjusted data is then provided for output.

22 Claims, 5 Drawing Sheets

DYNAMIC DATA-DRIVEN BIOLOGICAL STATE ANALYSIS

FIELD

This specification generally describes technology related to biomarker measurements, natural language processing and predictive modeling.

BACKGROUND

Dietary guidance regimens manage pathological risks such as weight gain or onset of diabetes by providing individualized recommendations to avoid certain physiological conditions that avoid such pathological risks, and promote other physiological conditions that reduce such pathological risks. For example, many dietary guidance regimens often track data indicating an amount of calories consumed by the user over a time period, medical history data indicating individualized risk factors (e.g., genetic predisposition to diabetes or high blood pressure), and/or other types of biometric data indicating physiological conditions of the user.

Systems that provide dietary guidance regimens to users often monitor specific biometric parameters that are descriptive of the user's biological state. For example, some systems monitor the amount of carbohydrate intake to adjust dietary guidance to avoid the onset of diabetes. Such systems often monitor measured levels of the biometric parameters over reoccurring time intervals. For example, a measured biomarker level can be compared to specified thresholds that indicate when a user is susceptible to pathological risks. In some instances, systems can provide automated recommendations to enable users to avoid certain user behavioral actions (e.g., consuming high number of carbohydrates), promote other user behavioral actions (e.g., participating in a daily exercise routine), or perform specified tasks to meet user goals (e.g., maintaining a daily caloric intake for a weight loss goal).

SUMMARY

Although many physiological recommendation systems can monitor levels of metabolic biomarkers in order to predict changes to a user's present biological state, such systems often cannot distinguish between changes that result based on the user's behavioral actions, changes that result based on the user's physiological conditions independent from the user's behavioral actions, or a combination of both. For example, unhealthy weight loss experienced by a user may be attributed to the user having recently experienced stressful event, or by maintaining an insufficient caloric intake to sustain the user's body weight. In this example, conventional systems would be capable of identifying the amount of weight lost and determine that the amount of weight lost creates health risks for the user by periodically monitoring different metabolic physiological parameters (e.g., body weight, body mass index (BMI)), and biomarkers (e.g., carbohydrate biomarkers, ketone biomarkers) over a time period. However, because these parameters and biomarkers do not capture information related indirect risk factors for pathological conditions (e.g., a user's mental stress level, behavioral activities, etc.), such systems are often incapable of identifying the various causes for risks that often underlie a pathological condition. As a result, such systems often fail to provide clinical recommendations that would sufficiently reduce a user's risk of incurring the pathological condition.

In some implementations, a system is capable of obtaining and processing both actively monitored and passively monitored data in parallel in order to improve the accuracy and the specificity by which pathological risks are identified for a user. For instance, actively monitored data indicating metabolic biomarker levels may be monitored in conjunction with passively monitored user activity data over a particular time period to enable the system to identify context-specific risk factors associated with changes to monitored metabolic biomarker levels. Conversational data or types of other activity data that are temporally related to changes in measured biomarker levels can be used by the system to identify a correlation for the change in biomarker levels. The system can then cross-correlate the two different types of monitored data to perform different actions. For example, the system can provide updated nutritional recommendations based on the cross-correlated data, change the type or frequency of collected biomarkers, among others.

Because passively monitored raw activity data often includes qualitative unstructured data, the system may use processing techniques to extract relevant information that is used to compare against monitored biomarker levels. For instance, the system may use natural language processing (NLP) techniques to parse text queries submitted by the user to identify terms that are determined to be associated with the particular biomarkers that are measured. In some instances, terms can be classified into particular topics that are descriptive of a user's mood or sentiment. In this regard, the identification of key words within historical queries submitted by the user (e.g., text messages sent to other users, search queries sent to a search engine, text input on a native application, etc.) can be used to identify a user's present mood or sentiment. Each topic can be associated with a particular score that indicates a probability that a corresponding mood/sentiment will beneficially or adversely impact a physiological condition associated with a measured biomarker level. In other instances, the system can use designated pre-computed term dictionaries that specify other types of language attributes descriptive of user behaviors, actions, and/or preferences. In this regard, the system uses NLP techniques to extract structured probabilistic data associated with user activity from a set of passively monitored activity data.

The system can use various statistical analysis techniques to correlate processed user activity data and monitored biomarker level data to identify an impact and/or change to a biological or physiological state for a user. For instance, the system can use machine learning and/or deep learning techniques to automatically identify an anticipated change to a present biological or physiological state for the user based a set of training data indicating known correlations between measured biomarker levels, user topics/sentiments, and changes to physiological condition. For example, training data may correlate a high caloric intake and high stress levels associated with a depression sentiment indicated by excessive usage of words of negative connotations with an increased risk of an associated physical order. In this example, the system can use pattern recognition to the training data to determine when measured biomarker data and user activity data indicates a high likelihood for a risk for the associated physical order.

Having identified correlations between user activity data and measured biomarker data, the system can then identify changes to a biological or physiological state and perform various actions to reduce pathological risks associated with the changes. The system accomplishes this with the use of a rule engine that specifies the performance of specific system actions in response to the satisfactions of certain conditions or triggers associated with each of the user activity data and the measured biomarker level data. In some instances, data obtained can be used to adjust a nutritional recommendation for a user to reduce risks. In such instances, an adjustment can initially be based on a measured biomarker level (e.g., high glucose or ketone intake), and then augmented based on a set of user preferences indicated by the user activity data (e.g., inputs indicating a positive preference towards certain types of food). In this regard, recommendations can be enhanced for the user based on determined correlations between the user activity data and the measured biomarker data as described above. In other instances, the adjustment can be changes to a monitoring regimen based either on a threshold level of change to a measured biomarker level or a specified user activity level indicated by a rule. Other types of adjustments are discussed in more detail below.

The system can utilize various learning techniques to dynamically adjust the monitoring techniques towards the actions, preferences, and/or biological states associated with a particular user. In some instances, this is accomplished by independently processing the measured biomarker level data and the user activity level data, and utilizing inferences from one type of data to dynamically augment the subsequent processing of the other type of data. For example, historical measured biomarker level data can be used to improve the processing of user activity data by parsing language information using term dictionaries that are associated with measured changes in biomarker levels (e.g., use of a diabetes term dictionary based on detecting periodic decreases in glucose level). In another example, the system may employ the use of learning algorithms to identify commonly used words and associate these words with corresponding changes to measured biomarker levels (e.g., within a shared time period), to generate a user-specific term dictionary that is then used to process both the subsequent instances of measured biomarker level data and user activity data. In both of these examples, the correlation of both types of data over time can be used to bi-directionally improve the processing of each type of data as time progresses and the system begins to automatically recognize certain patterns associated with each type of data.

In one general aspect, a computer-implemented method includes: obtaining, (i) data indicating measured levels of one or more metabolic biomarkers from one or more samples of the user over a particular time period, and (ii) activity data from a device associated with a user over the particular time period; determining a biological state for the user during the particular time period based at least on the measured levels of the one or more metabolic biomarkers; identifying (i) one or more user inputs indicated within the activity data, and (ii) for each of the one or more user inputs, scores reflecting respective likelihoods that a particular user input indicates a change to one or more aspects of the biological state for the user; adjusting data corresponding to the biological state for the user based at least on the one or more identified user inputs and the respective scores for each of the one or more user inputs; and providing, for output to the device associated with the user, a communication that is generated based on the adjusted data corresponding to the biological state.

Implementations may include one or more of the following features. For example, in some implementations, the activity data indicating interaction of the user with the device includes one or more text messages submitted by user on the device over the particular time period.

In some implementations, identifying the one or more user inputs indicated by within the activity data includes: identifying one or more terms included within the one or more text messages submitted by the user on the device based at least one parsing the one or more text messages; obtaining a set of terms that are predetermined to be associated with the biological state for the user during the particular time period; and determining that at least one of the one or more terms included within the one or more text messages submitted by the user is included within the set of terms that are predetermined to be associated with the biological state for the user during the particular time period.

In some implementations, the data indicating the measured levels of the one or more metabolic biomarkers includes at least a measured level of a glucose biomarker and a measured level of a ketone biomarker.

In some implementations, determining the biological state for the user during the particular time period includes: determining that at least one of the measured level of glucose biomarker and the measured level of ketone biomarker exceeds a corresponding predetermined threshold value within the one or more samples of the user; and in response to determining that at least one of the measured level of glucose biomarker or the measured level of ketone biomarker exceeds a corresponding predetermined threshold value within the one or more samples of the user, automatically determining that a carbohydrate intake of the user is above a metabolic tolerance for the user.

In some implementations, the data indicating the measured levels of the one or more metabolic biomarkers includes at least a measured level of palmitoleic acid and a measured level of dihomo-γ-linolenic acid within the one or more samples of the user.

In some implementations, determining the biological state for the user during the particular time period includes: determining that at least one of the measured level of palmitoleic acid or the measured level of dihomo-γ-linolenic acid exceeds a corresponding predetermined threshold value within the one or more samples of the user; and in response to determining that at least one of the measured level of palmitoleic acid or the measured level of dihomo-γ-linolenic acid exceeds a corresponding predetermined threshold value within the one or more samples of the user, automatically determining that a carbohydrate intake of the user is above a metabolic tolerance for the user.

In some implementations, adjusting data descriptive of a clinical recommendation includes automatically adjusting a dosage for a drug prescribed to the user.

In some implementations, adjusting data descriptive of a clinical recommendation includes adjusting a nutritional recommendation for a dietary plan for the user.

In some implementations, the one or more aspects of the biological state for the user includes at least one of a user-specific nutritional requirement to sustain a carbohydrate remission for the user, a weight loss goal specified for the user, or a communication provided to the user corresponding to the biological state for the user.

In some implementations, the data corresponding to the biological state for the user includes a clinical recommendation associated with the biological state for the user.

The details of one or more implementations are set forth in the accompanying drawings and the description below.

Other potential features and advantages will become apparent from the description, the drawings, and the claims.

BRIEF DESCRIPTION OF THE DRAWINGS

In the drawings, like reference numbers represent corresponding parts throughout.

DETAILED DESCRIPTION

Figure 1A:
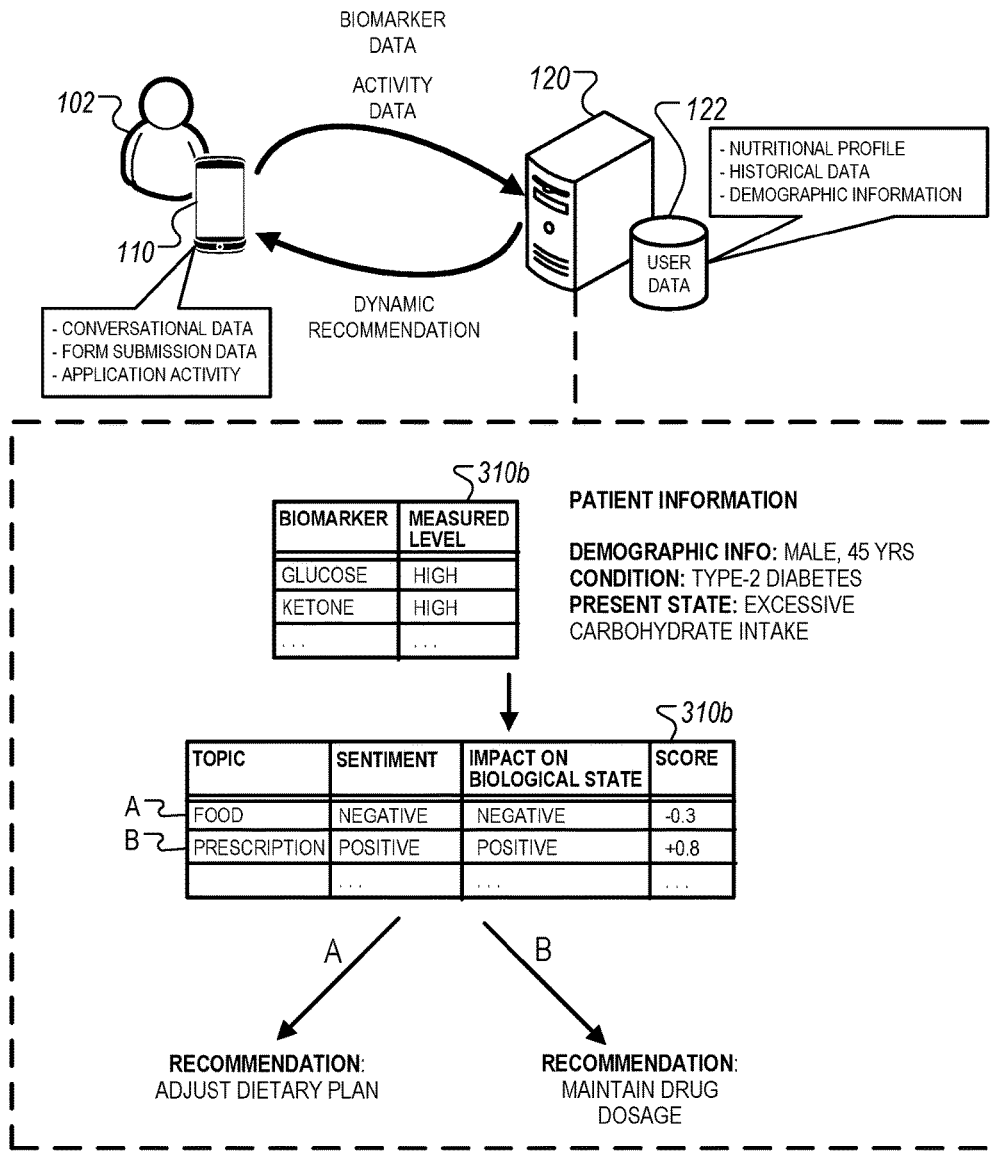
FIG. 1A is conceptual diagram that illustrates an example of a system for dynamically adjusting data associated with a user's biological state.

In general, a system is capable of obtaining and processing both actively monitored and passively monitored data in parallel in order to improve the accuracy and the specificity by which pathological risks are identified for a user. For instance, the system may process actively monitored data indicating metabolic biomarker levels can in conjunction with passively monitored user activity data over a shared time period. The system then identifies context-specific risk factors associated with changes to monitored metabolic biomarker levels. As an example, conversational data or other types of activity data that are temporally related to changes in measured biomarker levels can be used by the system to identify a specific cause for the change in biomarker levels. The system can then cross-correlate the two different types of monitored data to perform different actions. For example, the system can provide updated nutritional recommendations based on the cross-correlated data, change the type or frequency of collected biomarkers, among others.

As described throughout, "user engagement" refers generally to user's activity on the application. In some instances, "user engagement" refers to the input received on the application that is related to user activity on the application (e.g., user input provided on an application interface, or sensor data associated with user activity). In other instances, "user engagement" refers to the user's performance on a program that is provided on the application. The user's performance can be measured relative to a set of program criteria that describes the objective or purpose of the program (e.g., physical activity goals, lowering cholesterol). In this regard, the system can measure "user engagement" in order to identify communications to both improve a user's interactions on the application (e.g., number of user inputs provided on the application) and improve the user's performance on a program provided on the application.

As described throughout, a "biological state" refers to a particular condition associated with a user in relation to his/her medical history. At any instance in time, a user may be associated with different biological states that represent different aspects of the user's overall physical and/or mental wellbeing. For instance, biological states can be used to describe present physiological conditions, present psychological conditions, or present behavioral conditions. In addition, each biological state can be associated with different biomarkers that are used to indicate and/or measure the condition associated with a particular biological state. As an example, a biological state relating to "heart health," can be monitored by measuring biomarkers such as blood pressure, blood oxygen level, breathing rate among others. In another example, a biological state relating to carbohydrate remission for weight loss, may include measuring carbohydrate biomarkers to indicate a blood sugar level of the user, or a ketone biomarkers to monitor diabetic ketosis.

As described throughout, a "biomarker" or "biological marker" refers to objective indications of a biological state observed from outside the user. Biomarkers can relate to any substance, structure, or process that can be measured in the body or its products and influence or predict the incidence of outcome or disease. Biomarker measurements can be used not only to identify both the incidence and outcome of disease, but also the effects of treatments, interventions, and unintended environmental exposure, such as to chemicals or nutrients. As an example, monitoring of biomarkers levels in the context of dietary regimen (e.g., glucose biomarkers, ketone biomarkers) can be used identify when a user is in a ketogenic state for inducing weight loss. In addition, monitoring of glucose and ketone biomarkers can be used to distinguish between healthy weight loss and unhealthy weight loss that poses pathological risks to the user. Although biomarker level measured is described throughout in the context of dietary regimen for simplicity, the use of "biomarkers" is not strictly limited for this specific application.

FIG. 1A is conceptual diagram that illustrates an example of a system 100A for dynamically adjusting data associated with a user's biological state. The system 100A general includes a device 110 associated with a user 102, and a server 120 that periodically exchange communication over a network. The server 120 includes storage 122 for storing user data associated with the user 102.

In general, data exchange between the device 110 and the server 120 enables the system 100A to dynamically adjust data corresponding to a biological state of the user 102 based on processing biomarker data and activity data. For instance, the server 120 initially obtains the biomarker data and user activity data collected from the device 110. The server 120 then executes a set of statistical analysis techniques by comparing the obtained data in reference to historical user data stored within the storage 122. The server 120 then automatically determines any changes to a present biological state of the user 102, and in response, generates a dynamic recommendation that is targeted to reduce any potential pathological risks associated with the change in the biological state of the user 102.

As described throughout, because the recommendations are generated based on both measured biomarker levels and NLP of the user activity data, the system is capable of identifying changes to a biological state that are traditionally undetectable to recommendation systems that typically configured to only identify changes to measured biomarker levels. Examples of such changes include changes in user sentiment, mood, preferences. Other examples of changes can include changes in conversational topics of electronic communications associated with the user (e.g., emails, text messages, social media posts). For instance, detected language-based biological state descriptions within the electronic communications such as specific complaints by the user, descriptions of actions and/or treatments can be used to identify the changes in the conversational topics.

In addition, the NLP of the user activity data also enables the system 100A to identify confounding variables that superficially impact biomarker levels in order to reduce incorrect determinations relating to a biological state based on changes to measured biomarker levels alone. As an example, conversational data of the user 102 during a time period in which a measured biomarker level is increased can be used to identify a likely user context associated with the user 102. The identified context associated with the user 102 can then be used to provide alternative causes for the changes in measured biomarker levels that are not associated with problematic reoccurring user behaviors. Other examples are described in detail below.

The system 100A utilizes the obtained biomarker data and the user activity data to adjust a dynamic recommendation provided to the user 102 based upon processing information associated with each. For instance, as shown in 310a, the biomarker data can include measurements for two biomarkers such as glucose and ketone. In this example, glucose and ketone biomarkers can be used to monitor carbohydrate intake for a user that is presently participating in a carbohydrate-restricted diet due to being diagnosed with type-two diabetes. In this regard, the system 100A is used by the user 102 to track and monitor activities relating generally to diet, and more specifically, to the amount of carbohydrates consumed by the user 102 over specified time periods (e.g., hourly, daily, weekly).

The biomarker data includes measurements of certain biomarker levels are collected over reoccurring time intervals. As described above, biomarkers can refer any type of measurable substance, structure, or process that is used as an objective indication of a biological state. Examples of biomarkers can include physiological indicators (e.g., blood pressure, heart rate, blood sugar), or measurements of substances that are indicative of a disease condition (e.g., insulin, carbohydrates, ketones, etc.).

The user activity data includes various types of data that are descriptive of interactions between the user 102 and the user device 110. For example, the user activity data can include conversational data such as text messages sent to contacts, emails transmitted through an associated email address, posts/comments submitted over a social media network, among other types of communications data. In other examples, the user activity data can include form submission data that includes user input on electronic forms or surveys that are periodically provided on device 110 for the user to complete. In other examples, the user activity data can include user input data collected through native applications executed on the device 110 (e.g., click-tracking data, gaze tracking data, historical navigation data), among others.

Once the server 120 receives the biomarker data and the activity data, the server 120 initially processes raw user activity data in order to extract information that is determined to be relevant to the measured biomarker levels indicated within the table 310b. For instance, the server 120 may extract conversational data that includes certain terms that are associated with each of the measured biomarkers.

As an example, presence of terms related to food (e.g., "hungry," "stuffed," "yummy") within the user input data may be used to identify conversation data that is associated with measured glucose levels. In another example, the server 120 may process query log data that includes previous search queries submitted by the users, search results accessed by the user in response to submitting the search queries, among others. The server 120 may then identify entity terms (e.g., names of restaurants, or locations of interest) that are determined to be relevant to a user's eating habits. For instance, high calorie intake can be associated with location and query data indicating that the user 102 has been repeatedly searching for locations associated with fast food service. In yet another example, the server 120 may extract data indicating the user actions on certain applications. For instance, the server 120 may extract a list of applications that were used by the user 102 and are known to be associated with a particular biomarker (e.g., an application provided by a fast food franchise), or how the user 102 interacts with such applications (e.g., click-tracking data, number of queries sent, etc.).

After processing the user activity data, the server 120 then aggregates the processed user activity data over periods of time to correspond to the measurements of biomarker levels. For instance, if a particular biomarker is measured at daily intervals, then the processed user activity data can be aggregated for each day. In addition, the server 120 may also categorize and/or classify different types of activity data over a time period in order to generate a structured data set. For example, conversational data can be segmented from application data in order to identify distinct user behavioral patterns associated with each type of activity data. In the first instance, conversational data can be used to indicate terms used by the user 102 that are descriptive of a user mood or sentiment, whereas application data can be used to identify user actions that are descriptive of user preferences. In this example, the server 120 can then provide two types of input (e.g., conversational data, application data) into different statistical classifiers to identify two distinct user behavioral patterns.

Once the server 120 has aggregated and segmented the processed user activity data over a designated time period corresponding to the frequency of biomarker level measurements, the server 120 the identifies an impact to a present biological state of the user. For instance, as described above, because the biological state can be impacted by both a biomarker level and patterns indicated by the user activity, the server 120 may determine the overall impact on the biological state given the changes to measured biomarker levels and user activity patterns. For example, in some implementations, the server 120 may determine whether the measured biomarker level and the user activity data indicates a general change to a biological state. In other implementations, the server 120 may determine, based on comparing the measured biomarker level and the user activity data to predetermined thresholds associated with different biological states, whether the user has transitioned between two different biological states (e.g., from an emotionally satisfied state to an emotionally unsatisfied state).

The identified changes to the biological state can then be used to perform different designated system actions that are designed to, for example, improve the monitoring of the user. In some instances, the server 120 may utilize a rule-based engine that specifies a list of different rules that coordinate the performance of certain system actions based on detecting certain changes to one or more biological states of the user. In some examples, the system actions performed in response to a detected change in the user's biological state can include adjusting a clinical recommendation for the user, adjusting a prescribed drug dosage associated with a certain treatment condition, or providing one or more notifications to the user 102 or other users such as healthcare providers, authorized caretakers, among others.

In other instances, the identified changes to the biological state can also be used provide educational content that provides the user with information associated with the biological state change. For example, in response to an increase in the detected glucose level for the user, various types of electronic content (e.g., dietary instructions that provide techniques to reduce sugar intake, health-associated risks of diabetes, etc.) may be presented to the user to notify him/her of the potential health-related implications of high sugar intake. The transmitted electronic content by accompanied by various types of instructions that attempt to influence the user's behavior in response to receiving the electronic content. For example, the system my identify an effective technique to provide the electronic content by adjusting the presentation of content (e.g., displaying text vs. displaying images), the arrangement of content, or the manner in which the content is provided to the user (e.g., sending a text message, generating a system notification, sending a text message, etc.). In this example, the system may determine the specific content presentation technique that is most effective based on previously detected user activity, interaction, and/or behavioral data.

Referring now to the example illustrated in FIG. 1A, the system 100 can be used to assist the user 102 in participating in a weight loss program. In general, the system 100 provides the user with recommendations to improve the user's progress based on monitoring biomarker levels of the user 102 and user activity data collected by the user device 110 of the user 102. Such recommendations can include adjustments to the user's dietary plan, or effective drug dosages to maximize healthy weight loss while minimizing pathological risks associated with the weight loss.

The server 120 initially receives biomarker data indicating that the user's measured glucose and ketone levels are high. Based upon these measurements, the server 120 then determines that the present biological state for the user is "EXCESSIVE CARBOHYDRATE INTAKE." In some instances, this determination is augmented based on other types of patient information such as the demographic information, or medical conditions associated with the patient record. In the example depicted in FIG. 1A, the user 102 has type-2 diabetes and is a male of 45 years, which increases the likelihood that user's present biological state is due to the medical condition.

The server 120 then extracts user activity data collected over a particular time period corresponding to from which biomarker levels were last measured (e.g., since the measurement taken from the previous day). As described above, the server 120 processes the user activity data using NLP techniques in order to identify topics to segment the different types of activity data. For each topic, the server 120 then uses one or more statistical classifiers to identify a whether the data is associated with a positive or negative sentiment. In this example, a positive sentiment is identified if user activity data indicates that the user has used terms with a positive linguistic connotation (e.g., "joyful," "enthusiastic," etc.), whereas a negative sentiment is identified if the user activity data indicates that the user has used terms with a negative linguistic connotation (e.g., "upset," "critical," etc.).

The server 120 also determines an anticipated impact on the biological state based on the identified sentiment for each topic. In some instances, in addition to the type of impact (e.g., positive or negative) that a topic is expected to have on a present biological state, the server 120 can also compute a magnitude of impact using a set of weighted scores. For example, topic A, which is associated with a negative sentiment, is determined to have a negative impact on the biological state, which is reflected in a negatively biased score of "−0.3." In comparison, topic B, which is associated with a positive sentiment, is determined to have a positive impact on the biological state, which is reflected in a positively biased score of "+0.8." In this example, the impact of the user activity data associated with topic B is determined to be more than double than that of the user activity associated with topic A. This can be because, for example, the terms associated with topic B have a strong positive connotation (e.g., "amazing!") whereas the terms associated with topic A have a mild to moderately negative connotation (e.g., "tolerable"). In another example, this can be because user activity associated with topic A can reflects a high positive user preference (e.g., repeat queries for performing certain activities), whereas user activity associated with topic B reflects a neutral to mildly negative preference (e.g., detected user input to avoid performing certain activities).

The determined impact on the biological state is then used to generate different clinical recommendations related to the program followed by the user 102. As described above, the recommendation is based on correlating measured biomarker levels in table 310*a* and the structured user activity data in table 310*b*. In the first example with respect to topic A, the server 120 determines to adjust a dietary plan associated with the topic "food" because the associated user sentiment indicates that the associated user activity is negative. In this example, a negative user sentiment can be used to infer that the present dietary plan suggested to the user is ineffective because the user's activity indicates an aversion. As a result, the server 120 automatically recommends an adjustment to a dietary plan associated with the program.

In contrast, in the second example with respect to topic B, the server 120 determines to maintain a current drug dosage associated with the topic "prescription" because the associated user sentiment indicates that the associated user activity is positive. In this example, a positive user sentiment can be used to infer that the present drug dosage suggested to the user is effective because the user's activity in relation to prescription behaviors is either neutral or positive. Examples of such behaviors can include data indicating that the user in complying with a prescribed treatment routine, or short time delays between a user being presented with a reminder to take a prescribed medication and the user actually taking the prescribed medication. As a result, the server 120, in this example, provides a recommendation to maintain the current drug dosage.

The two examples described above illustrate how biomarker data and user activity data can processed and analyzed in parallel in order to obtain granular information associated with a user's participation within a health monitoring program. The measured biomarker levels provide an objective indication of the user's biological state (e.g., physiological conditions) whereas the collected user activity data provide a subjective, user-specific indication of different aspects of the user's biological state that are not entirely reflected within the measured biomarker levels. As a result, by collecting, processing, and analyzing both types of data, the system 100 is capable of both acutely understanding changes and/or impacts to the biological state that can potentially cause pathological risks to the user, but also perform automated actions to reduce the likelihood of the user incurring additional pathological risks.

Figure 1B:
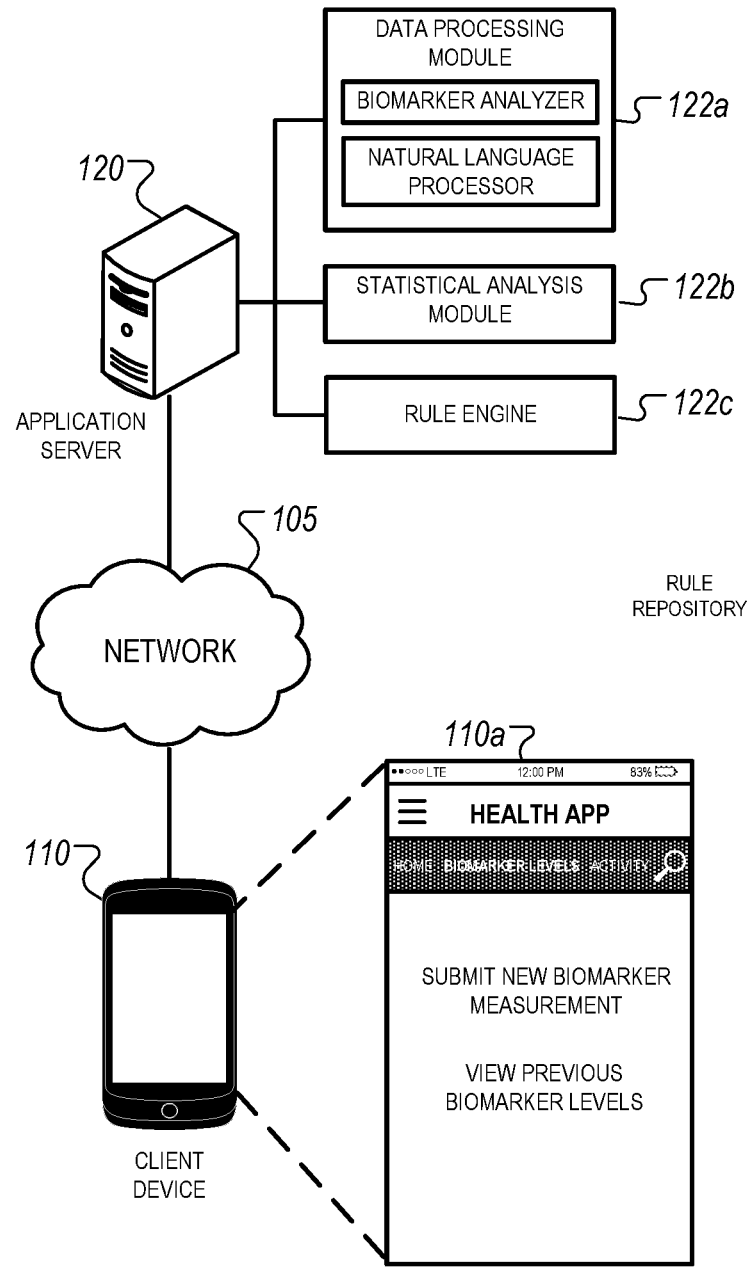
FIG. 1B is a block diagram that illustrates an example of a system that is capable of dynamically adjusting data associated with a user's biological state.

FIG. 1B is a block diagram that illustrates an example of a system 100B that is capable of dynamically adjusting data associated with a user's biological state. The system 100B generally includes the client device 110 and the server 120 connected over a network 105. The server 120 includes a data processing module 122*a*, a statistical analysis module 122b, and a rule engine 122c, which all process and analyze biomarker data and user activity data collected on the client device 110. The processed information is used by the server 120 to generate recommendations that are then provided for output on an application 110a that is displayed on the client device 110.

The client device 110 can be any type of personal electronic computing device with an associated screen or display for providing the application 110a for output to the user 102. For example, the client device 110 can be one or more of a smartphone, a laptop computing device, a tablet computing device, a wearable electronic device, a desktop computing device, among other types of devices.

The data processing module 122a further includes a biomarker analyzer for processing biomarker data, and a natural language processor for processing various types of activity data included within the obtained user activity data. In some implementations, the natural language processor is capable of parsing individual text segments included within conversational data obtained from the client device 110 (e.g., text messages, emails, memos, etc.) and identifying specific terms or phrases are likely to be descriptive of a context associated with the user. Examples of context data include a present application used by the user, a type of activity performed by the user, a user location, among other types of information that other than the user's physiological condition as indicated by the biomarker data.

The statistical analysis module 122b processes the biomarker data and the user activity data in parallel, as described above with respect to FIG. 1A, in order to derive statistical inferences that are then used to provide dynamic recommendations to the user. In some implementations, the statistical analysis module 122b may include a neural network, as depicted in more detail in FIG. 2, that is capable of identifying different sub-states for a user based on the biomarker data and user activity data received on the client device 110. For example, the statistical analysis module 122b can be configured to predict a certain sub-state for the user at a particular time point based on comparing attributes indicated within the received biomarker data and user activity data to known attributes indicated by training data associated with each sub-state. In this example, the statistical analysis module 122b may use supervised or unsupervised learning techniques, e.g., classification and regression, in order to predict a sub-state.

In some implementations, the statistical analysis module 122b may user other types of suitable deep learning techniques aside from neural networks to derive statistical inferences. For example, the statistical analysis module 122b may be capable of using support vector machines, clustering techniques, object and/or category classifiers, among other types of machine learning techniques.

The rule engine 122c enables the data processing module 122a and the statistical analysis module 122b to identify applicable rules that are associated with the received biomarker data and the user activity data, and determine whether one or more conditions specified by the applicable rules have been satisfied. In general, the rule engine 122c may access a repository of rules that each specify different triggers and/or conditions associated with biomarker data and user activity data, and an associated conclusion and/or action to be performed. As an example, a particular rule may specify a threshold glucose level, the satisfaction of which, results in a conclusion that the user has had excessive carbohydrate intake. In another example, another rule may specify that detection of terms that are associated with food and also have a negative connation within the user activity data results in a conclusion that a dietary regimen specified by a health management program for the user is ineffective.

In addition, the rule engine 122c may periodically update and adjust the rules specified within the rule repository based upon newly received biomarker data and/or user activity data. For instance, the rule engine 122c may add new rules that are descriptive new user behaviors, conditions, or activities, delete rules that are determined to no longer be relevant, or adjust existing rules that specify conditions that are not likely to be relevant to the user's present condition. For example, a specified threshold for a biomarker level may be reduced if past biomarker measurement levels over a time period indicate a slow decrease in average measured biomarker levels. In another example, if the user initiates a new phase of a treatment program that specifies new compliance and/or behavioral requirements, then rules associated with the prior phase of the treatment program may be disregarded by the rule engine 122c.

Although the example in FIG. 1A illustrates a technique that uses a rule engine to determine whether one or more conditions specified by the applicable rules have been satisfied, in some implementations, other types of determination techniques can be used. For instance, the system may use various types of machine learning techniques described throughout to identify the occurrence of changed user conditions, and performing actions responsive to the changed user conditions.

Figure 2:
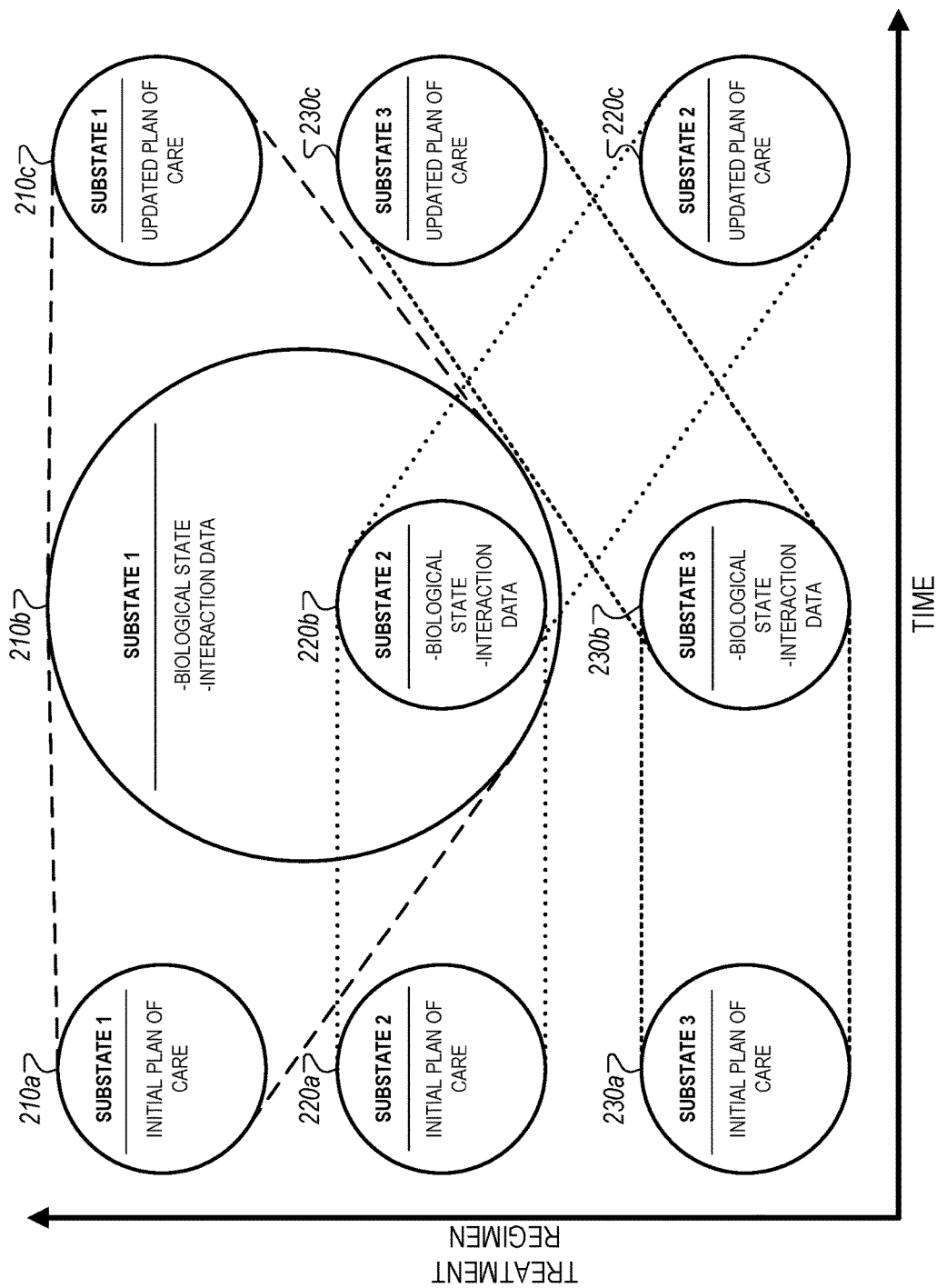
FIG. 2 is a conceptual diagram that illustrates different sub-states within a neural network architecture that correspond to various biological states for the user.

FIG. 2 is a conceptual diagram that illustrates different sub-states within a neural network architecture that correspond to various biological states for the user. In the figure, the horizontal axis represents a progression of time reflective of the amount of time a user participates in a particular health management program. The vertical axis represents a treatment regimen that specifies different plans of care for different biological sub-states determined for a user. As an example, different sub-states can represent different physiological conditions for the user, and their corresponding plans of care can specify clinical treatments for respective pathologies associated with each sub-state.

In general, the techniques described above with respect to FIGS. 1A and 1B, can be utilized to dynamically adjust various aspects of the treatment regimen over a time period. For instance, various types of machine learning and/or deep learning techniques may be used to determine a biological sub-state for a user, a suitable plan of care for the determined biological sub-state, and provide any adjustments to content provided to the user.

As an example, one change can be represented as a change to the plan of care for a particular sub-state based on received biomarker data and/or user activity data (e.g., between sub-states 210a and 210c, 220a and 220c, and 230a and 230c). In another example, a change can be represented as to how a sub-state is monitored in relation to other sub-states within the entire treatment regimen. In this example, the initial prioritization for sub-state monitoring may be sub-state 210a, followed by sub-state 220a, and then finally, sub-state 230a. However, once biomarker data and user activity data is received over time, the prioritizations for sub-states 220a and 220b can be adjusted such that, at a later point in time, the prioritization for sub-state monitoring is updated to be sub-state 210c, followed by sub-state 230c, and then finally, sub-state 220c. As an illustration of this example, if a treatment regimen for a particular disease specifies the monitoring of three co-occurring pathologies, then disease progression over time can be used to automatically adjust the real-time prioritization of the three individual pathologies. In this illustration, received biomarker data and user interaction data can be used to predict and/or automatically identify disease progression as a means of providing an automated clinical recommendation.

In another example, scope of a sub-state within a treatment regimen can be adjusted based on the biological state determined for the user based on the received biomarker data. In the figure, the scope of the initial sub-state 210a is initially expanded such that the initial sub-state 220a becomes a species sub-state 220b of the expanded sub-state 210b. As an illustration of this concept, the expansion of a particular pathology (e.g., cancer metastases) can cause multiple impacts on a patient's biological state such that monitoring of the particular pathology, after its expansion, can related to the monitoring of other pathologies that are more limited in scope.

Figure 3:
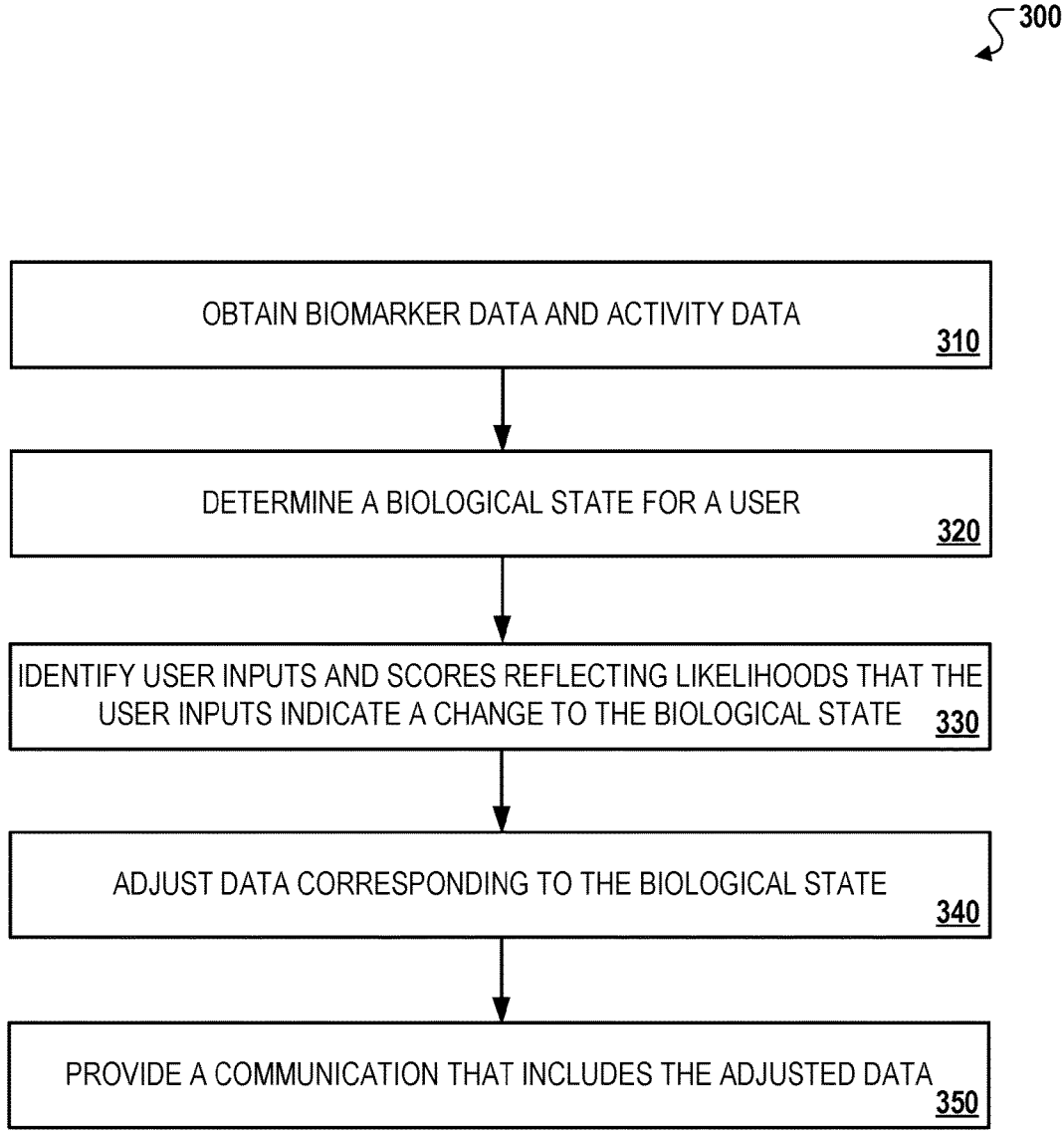
FIG. 3 is a flowchart that illustrates an example of a process for dynamically adjusting data associated with a user's biological state.

In summary, FIG. 3 illustrates that analysis of the biomarker data and the user interaction data can be used to dynamically adjust the monitoring requirements, priorities and/or conditions can be dynamically over time. In this regard, the biomarker data and the user interaction data can be used to improve techniques to reduce occurrence of disease pathologies by providing various means of adjusting ineffective or irrelevant monitoring techniques based on a patient's present condition.

FIG. 3 is a flowchart 300 that illustrates an example of a process 300 for dynamically adjusting data associated with a user's biological state. Briefly, the process may include obtaining biomarker data and activity data (310), determining a biological state for a user (320), identifying user inputs and scores reflecting likelihoods that the user inputs indicate a change to the biological state (330), adjusting data corresponding to the biological state (340), and providing a communication that includes the adjusted data (350).

In more detail, the process may include obtaining biomarker data and activity data (310). For instance, the user device 110 or the server 120 may obtain data indicating measured levels of one or more metabolic biomarkers from one or more samples of the user 102 over a particular time period. The user device 110 or the server 210 may also obtain activity data from the user device 110 over the particular time period. As depicted above in table 310b, the biomarker data can include measured levels for a set of monitored biomarkers such as glucose and ketone levels. In addition, the user activity data can include conversational data, form submission data, or other types of activity data of the user 102 on the user device 110.

The process 300 may include determining a biological state for a user (320). For instance, the user device 110 or the server 120 may determine a biological state for the user 102 during the particular time period based at least on the measured levels of the one or more metabolic biomarkers. For example, a high glucose level can be used to indicate that the biological state for the user 102 is excessive carbohydrate intake.

The process 300 may include identifying user inputs and scores reflecting likelihoods that the user inputs indicate a change to the biological state (330). For instance, the user device 110 or the server 120 may identify one or more user inputs indicated within the activity data, (e.g., text messages sent, webpages accessed, emails received, etc.). For each of the one or more user inputs, the user device 110 or the server 120 may compute scores reflecting respective likelihoods that a particular user input indicates a change to one or more aspects of the biological state determined in step 320. For example, as illustrated in FIG. 1A, user inputs related to the topic of "FOOD" can analyzed to determine a score of "−0.3," reflecting a negative impact on the biological state for the user 102. Alternatively, user inputs related to the topic of "PRESCRIPTION" can be analyzed to determine a score of "+0.8," reflecting a positive impact on the biological state for the user 102. In these examples, the respective scores can be determined using various natural language processing techniques to identify the sentiment associated with each type of input.

The process 300 may include adjusting data corresponding to the biological state (340). For instance, the user device 110 or the server 120 may adjust data corresponding to the biological state for the user 102 based at least on the one or more identified user inputs and the respective scores for each of the one or more user inputs. As described above with respect to FIG. 1A, in one example, the user inputs related to the topic of "FOOD" and their corresponding negative score can be used to determine that the current dietary plan associated with the biological state is insufficient and/or otherwise not preferable to the user. In response, the user device 110 or the server 120 may generate an adjusted dietary plan for a treatment regimen that the user 102 is currently participating in.

The process 300 may include providing a communication that includes the adjusted data (350). For instance, the user device 110 or the server 120 may provide a communication that includes the adjusted data corresponding to the biological state for output to the user device 110. For example, as described above with respect to step 340, an adjusted dietary plan for the treatment regimen that the user 102 is currently participating in can be included in a communication that is then provided as an update through a native application that runs on the user device 110.

Figure 4:
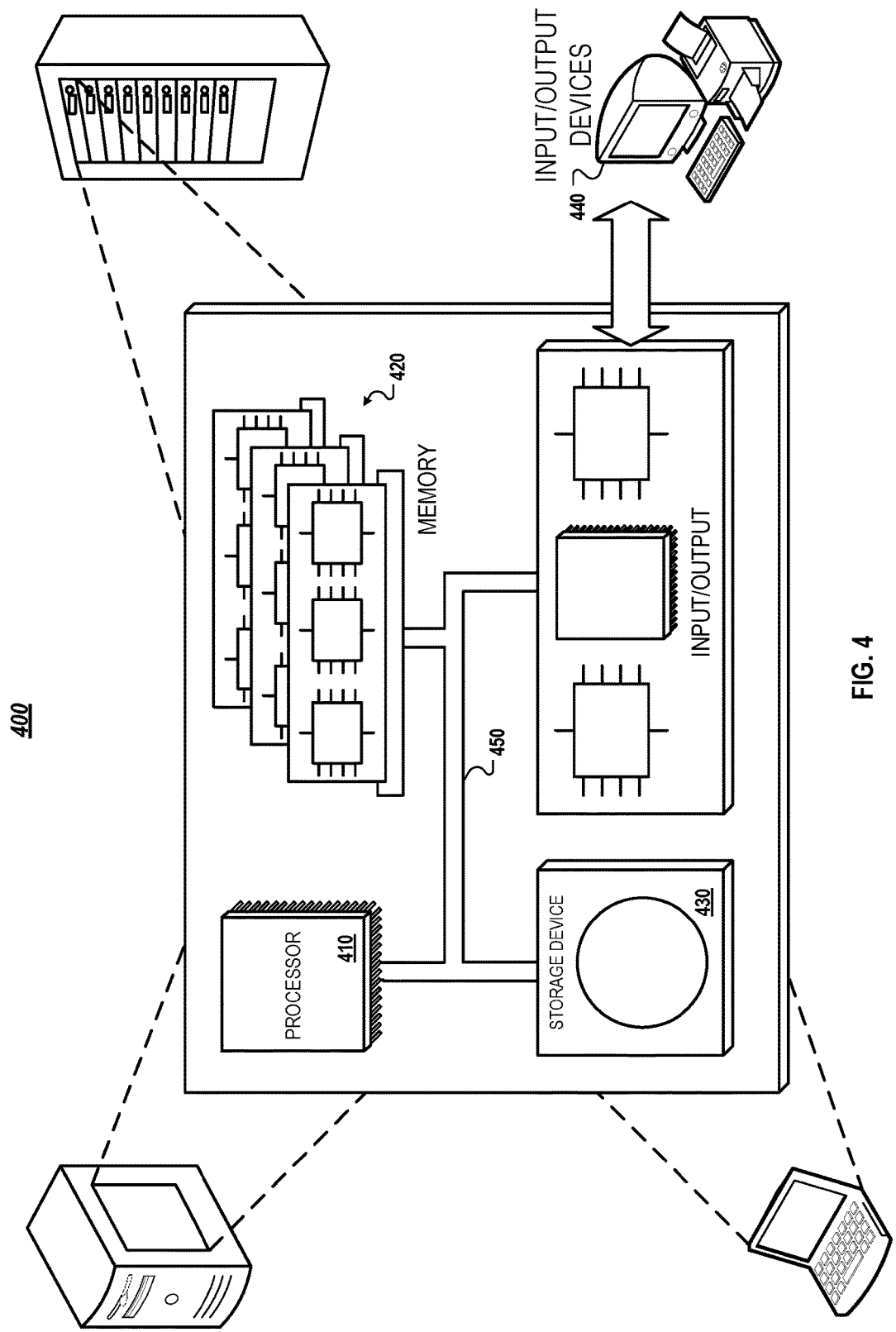
FIG. 4 is a block diagram of computing devices on which the processes described herein, or portions thereof, can be implemented.

FIG. 4 is a schematic diagram of an example of a generic computer system 400. The system 400 can be used for the operations described in association with FIGS. 1-6 according to some implementations. The system 400 may be included in the systems 100 and 200.

The system 400 includes a processor 410, a memory 420, a storage device 430, and an input/output device 440. Each of the components 410, 420, 430, and 440 are interconnected using a system bus 450. The processor 410 is capable of processing instructions for execution within the system 400. In one implementation, the processor 410 is a single-threaded processor. In another implementation, the processor 410 is a multi-threaded processor. The processor 410 is capable of processing instructions stored in the memory 420 or on the storage device 430 to display graphical information for a user interface on the input/output device 440.

The memory 420 stores information within the system 400. In one implementation, the memory 420 is a computer-readable medium. In one implementation, the memory 420 is a volatile memory unit. In another implementation, the memory 420 is a non-volatile memory unit.

The memory 420 stores information within the system 400. In one implementation, the memory 420 is a computer-readable medium. In one implementation, the memory 420 is a volatile memory unit. In another implementation, the memory 420 is a non-volatile memory unit.

The storage device 430 is capable of providing mass storage for the system 400. In one implementation, the storage device 430 is a computer-readable medium. In various different implementations, the storage device 430 may be a floppy disk device, a hard disk device, an optical disk device, or a tape device.

The input/output device 440 provides input/output operations for the system 400. In one implementation, the input/output device 440 includes a keyboard and/or pointing device. In another implementation, the input/output device 440 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

A number of embodiments have been described. Nevertheless, it will be understood that various modifications may be made without departing from the spirit and scope of the invention. In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method performed by one or more computers, the method comprising:
   obtaining, by a server system and from a computing device of a user, biomarker data indicating measured levels of one or more metabolic biomarkers from one or more samples of the user over a particular time period;
   determining, by the server system, a biological state for the user during the particular time period based at least on the measured levels of the one or more metabolic biomarkers;
   obtaining, by the server system and from the computing device, text messages submitted by the user through the computing device over the particular period of time;
   identifying, by the server system, conversational features representing one or more terms included in the text messages of the user, wherein the conversational features are identified as being associated with the biological state determined for the user;
   classifying, by the server system and using a machine learning module, the conversational features as corresponding to a particular conversational pattern from among multiple conversational patterns associated with the biological state, wherein the machine learning module is trained to predict a conversational pattern represented by the one or more terms based on the biomarker data and historical account data of the user;
   determining, by the server system and based on the classification of the one or more terms, behavioral activity patterns corresponding to the particular conversational pattern, the behavioral activity patterns comprising
      a first behavioral activity pattern representing an overall emotional sentiment of the user during the particular period of time and
      a second behavioral activity pattern indicating actions performed by the user during the particular period of time;

determining, by the server system, respective likelihoods that the behavioral activity parameters and the measured levels of the one or more metabolic biomarkers indicate a predicted change to the biological state;
selecting, by the server system and based on the determined likelihoods that the behavioral activity parameters and the measured levels of the one or more metabolic biomarkers indicate a predicted change to the biological state, content to include in a communication from among different types of content; and
providing, by the server system and for output to the computing device, the communication that includes the selected content.

2. The method of claim 1, wherein the biomarker data indicating the measured levels of the one or more metabolic biomarkers comprises at least a measured level of a glucose biomarker and a measured level of a ketone biomarker.

3. The method of claim 2, wherein determining the biological state for the user during the particular time period comprises:
determining that at least one of the measured level of glucose biomarker and the measured level of ketone biomarker exceeds a corresponding predetermined threshold value within the one or more samples of the user; and
in response to determining that at least one of the measured level of glucose biomarker or the measured level of ketone biomarker exceeds a corresponding predetermined threshold value within the one or more samples of the user, automatically determining that a carbohydrate intake of the user is above a metabolic tolerance for the user.

4. The method of claim 1, wherein the biomarker data indicating the measured levels of the one or more metabolic biomarkers comprises at least a measured level of palmitoleic acid and a measured level of dihomo-γ-linolenic acid within the one or more samples of the user.

5. The method of claim 4, wherein determining the biological state for the user during the particular time period comprises:
determining that at least one of the measured level of palmitoleic acid or the measured level of dihomo-γ-linolenic acid exceeds a corresponding predetermined threshold value within the one or more samples of the user; and
in response to determining that at least one of the measured level of palmitoleic acid or the measured level of dihomo-γ-linolenic acid exceeds a corresponding predetermined threshold value within the one or more samples of the user, automatically determining that a carbohydrate intake of the user is above a metabolic tolerance for the user.

6. The method of claim 5, wherein the selected content that is included in the communication comprises a dosage for a drug prescribed to the user.

7. The method of claim 5, wherein the selected content that is included in the communication comprises a nutritional recommendation for a dietary plan for the user.

8. The method of claim 1, wherein the predicted change to the biological state for the user comprises at least one of a user-specific nutritional requirement to sustain a carbohydrate remission for the user, a weight loss goal specified for the user, or a communication provided to the user corresponding to the biological state for the user.

9. The method of claim 1, wherein:
the machine learning module comprises a neural network trained to identify an overall sentiment indicated by the one or more terms within the text messages; and
the one or more behavioral activity parameters associated with the biological state comprises the overall sentiment identified by the neural network.

10. The method of claim 9, wherein identifying the overall sentiment indicated by the one or more terms within the text messages comprises:
obtaining, by the neural network, data indicating (i) a collection of terms, and (ii) a predetermined sentiment corresponding to each term included within the collection of terms; and determining that a particular set of terms within the text messages are included within the collection of terms; and
determining the overall sentiment based on predetermined sentiments of terms within the particular set of terms.

11. The method of claim 1, wherein the one or more behavioral activity parameters comprises a parameter representing a frequency of use of a set of predetermined terms by the user over the particular period of time.

12. The method of claim 1, wherein determining the respective likelihoods that the behavioral activity parameters indicate a predicted change to the biological state comprises:
selecting a subset of rules from a set of rules that are determined by the server system to correspond to the behavioral activity parameters, each rule within the set of rules being associated with one or more triggers and one or more conditions that indicate a change to the biological state.

13. The method of claim 12, further comprising:
determining that the biomarker data or the one or more terms included in the text messages satisfies at least one trigger or at least one condition for a particular rule from among the selected subset of rules; and
in response to determining that the biomarker data or the one or more terms included in the text messages satisfies at least one trigger or at least one condition for the particular rule, determining a high likelihood that a particular behavioral activity pattern corresponding to the particular rule indicates a predicted change to the biological state.

14. The method of claim 1, wherein:
the predicted change to the biological state represents a predicted transition from a first sub-state of the biological state to a second sub-state of the biological state, wherein:
the first sub-state is associated with a first set of treatment conditions for a pathology associated with the biological state;
the second sub-state is associated with a second set of treatment conditions for the pathology associated with the biological state;
the selected content that is included in the communication comprises data corresponding to the second set of treatment conditions for the pathology associated with the biological state.

15. The method of claim 1, wherein:
the conversational features representing one or more terms included in the text messages of the user comprises word vectors of the one or more terms; and
the particular conversational pattern that corresponds to the conversational features representing the one or more terms comprises a linguistic connotation associated with the biological state determined for the user.

16. A system comprising:
one or more computers that include a server system; and
a non-transitory computer-readable medium coupled to the one or more computers having instructions stored thereon, which, when executed by the one or more computers, cause the one or more computers to perform operations comprising:
- obtaining, by a server system and from a computing device of a user, biomarker data indicating measured levels of one or more metabolic biomarkers from one or more samples of the user over a particular time period;
- determining, by the server system, a biological state for the user during the particular time period based at least on the measured levels of the one or more metabolic biomarkers;
- obtaining, by the server system and from the computing device, text messages submitted by the user through the computing device over the particular period of time;
- identifying, by the server system, conversational features representing one or more terms included in the text messages of the user, wherein the conversational features are identified as being associated with the biological state determined for the user;
- classifying, by the server system and using a machine learning module, the conversational features as corresponding to a particular conversational pattern from among multiple conversational patterns associated with the biological state, wherein the machine learning module is trained to predict a conversational pattern represented by the one or more terms based on the biomarker data and historical account data of the user;
- determining, by the server system and based on the classification of the one or more terms, behavioral activity patterns corresponding to the particular conversational pattern, the behavioral activity patterns comprising
  - a first behavioral activity pattern representing an overall emotional sentiment of the user during the particular period of time and
  - a second behavioral activity pattern indicating actions performed by the user during the particular period of time;
- determining, by the server system, respective likelihoods that the behavioral activity parameters and the measured levels of the one or more metabolic biomarkers indicate a predicted change to the biological state;
- selecting, by the server system and based on the determined likelihoods that the behavioral activity parameters and the measured levels of the one or more metabolic biomarkers indicate a predicted change to the biological state, content to include in a communication from among different types of content; and
- providing, by the server system and for output to the computing device, the communication that includes the selected content.

17. The system of claim 16, wherein the biomarker data indicating the measured levels of the one or more metabolic biomarkers comprises at least a measured level of a glucose biomarker and a measured level of a ketone biomarker.

18. The system of claim 17, wherein determining the biological state for the user during the particular time period comprises:
- determining that at least one of the measured level of glucose biomarker and the measured level of ketone biomarker exceeds a corresponding predetermined threshold value within the one or more samples of the user; and
- in response to determining that at least one of the measured level of glucose biomarker or the measured level of ketone biomarker exceeds a corresponding predetermined threshold value within the one or more samples of the user, automatically determining that a carbohydrate intake of the user is above a metabolic tolerance for the user.

19. A non-transitory computer-readable medium storing software comprising instructions executable by one or more computers which, upon such execution, cause the one or more computers to perform operations comprising:
- obtaining, by a server system and from a computing device of a user, biomarker data indicating measured levels of one or more metabolic biomarkers from one or more samples of the user over a particular time period;
- determining, by the server system, a biological state for the user during the particular time period based at least on the measured levels of the one or more metabolic biomarkers;
- obtaining, by the server system and from the computing device, text messages submitted by the user through the computing device over the particular period of time;
- identifying, by the server system, conversational features representing one or more terms included in the text messages of the user, wherein the conversational features are identified as being associated with the biological state determined for the user;
- classifying, by the server system and using a machine learning module, the conversational features as corresponding to a particular conversational pattern from among multiple conversational patterns associated with the biological state, wherein the machine learning module is trained to predict a conversational pattern represented by the one or more terms based on the biomarker data and historical account data of the user;
- determining, by the server system and based on the classification of the one or more terms, behavioral activity patterns corresponding to the particular conversational pattern, the behavioral activity patterns comprising
  - a first behavioral activity pattern representing an overall emotional sentiment of the user during the particular period of time and
  - a second behavioral activity pattern indicating actions performed by the user during the particular period of time;
- determining, by the server system, respective likelihoods that the behavioral activity parameters and the measured levels of the one or more metabolic biomarkers indicate a predicted change to the biological state;
- selecting, by the server system and based on the determined likelihoods that the behavioral activity parameters and the measured levels of the one or more metabolic biomarkers indicate a predicted change to the biological state, content to include in a communication from among different types of content; and
- providing, by the server system and for output to the computing device, the communication that includes the selected content.

20. The non-transitory computer-readable medium of claim 19, wherein the biomarker data indicating the measured levels of the one or more metabolic biomarkers comprises at least a measured level of a glucose biomarker and a measured level of a ketone biomarker.

21. The non-transitory computer-readable medium of claim 20, wherein determining the biological state for the user during the particular time period comprises:
   determining that at least one of the measured level of glucose biomarker and the measured level of ketone biomarker exceeds a corresponding predetermined threshold value within the one or more samples of the user; and
   in response to determining that at least one of the measured level of glucose biomarker or the measured level of ketone biomarker exceeds a corresponding predetermined threshold value within the one or more samples of the user, automatically determining that a carbohydrate intake of the user is above a metabolic tolerance for the user.

22. The method of claim 19, wherein:
the interaction data identifies a first type of interaction of the user with the computing device and a second type of interaction of the user with the computing device that is different from the first type of interaction;
classifying the interaction data comprises:
   selecting, from among a plurality of statistical classifiers, (i) a first statistical classifier based on the first type of interaction of the user with the computing device, and (ii) a second statistical classifier based on the second type of interaction of the user with the computing device, the second statistical classifier configured to apply a different set of classification rules than the first statistical classifier;
   identifying, using the first statistical classifier, a first set of behavioral activity parameters associated with the biological state for the first type of interaction, and
   identifying, using the second statistical classifier, a second set of behavioral activity parameters associated with the biological state for the second type of interaction.

* * * * *